United States Patent
Ciupik et al.

(10) Patent No.: US 9,017,383 B2
(45) Date of Patent: Apr. 28, 2015

(54) UNLOADING D-DYNAMIC INTERVERTEBRAL DEVICE

(75) Inventors: Lechoslaw Ciupik, Zielona Góra (PL); Agnieszka Kierzkowska, Polkowice (PL)

(73) Assignee: LfC Sp. z o.o., Zielona Gora (PL)

(*) Notice: Subject to any disclaimer, the term of this patent is extended or adjusted under 35 U.S.C. 154(b) by 39 days.

(21) Appl. No.: 12/900,787

(22) Filed: Oct. 8, 2010

(65) Prior Publication Data

US 2011/0087286 A1    Apr. 14, 2011

(30) Foreign Application Priority Data

Oct. 9, 2009 (PL) .......................................... 389241

(51) Int. Cl.
*A61B 17/70* (2006.01)

(52) U.S. Cl.
CPC .................. *A61B 17/7065* (2013.01)

(58) Field of Classification Search
CPC ........... A61B 17/7065; A61B 17/7067; A61B 17/7068
USPC ......... 606/248, 249, 258, 250–257, 259–261, 606/246, 247; 623/17.15, 17.11, 17.16
See application file for complete search history.

(56) References Cited

U.S. PATENT DOCUMENTS

| | | | |
|---|---|---|---|
| 4,611,582 A | 9/1986 | Duff | |
| 5,261,908 A * | 11/1993 | Campbell, Jr. | 606/279 |
| 5,439,463 A | 8/1995 | Lin | |
| 5,885,284 A * | 3/1999 | Errico et al. | 606/252 |
| 6,592,585 B2 * | 7/2003 | Lee et al. | 606/252 |
| 7,883,532 B2 * | 2/2011 | Biscup et al. | 606/324 |
| 2006/0241614 A1 | 10/2006 | Bruneau et al. | |
| 2006/0293662 A1 * | 12/2006 | Boyer et al. | 606/61 |
| 2007/0100340 A1 * | 5/2007 | Lange et al. | 606/61 |
| 2007/0196166 A1 * | 8/2007 | Rogeau et al. | 403/120 |

(Continued)

FOREIGN PATENT DOCUMENTS

| | | |
|---|---|---|
| WO | 0191658 A1 | 12/2001 |
| WO | 2007127550 A2 | 11/2007 |

(Continued)

OTHER PUBLICATIONS

International Preliminary Report on Patentability and Written Opinion, dated Apr. 12, 2012, regarding International Application No. PCT/PL2010/000101; Applicant: LfC Spolka Z o.o.

(Continued)

*Primary Examiner* — Jan Christopher Merene
*Assistant Examiner* — Atiya Mahmud
(74) *Attorney, Agent, or Firm* — Hovey Williams LLP

(57) ABSTRACT

An unloading dynamic intervertebral device comprising a first bar and a second bar configured for providing an even, steady and adjustable decompression of the intervertebral interspinous space and for maintaining the distance between at least two vertebrae. The first bar may comprise a guideline with an elongated gap formed therein. The second bar may comprise a guide having at least one tang interposed within the elongated gap of the first bar, such that the first bar and the second bar are rotationally and slidably connected with each other about the tang. An end of the first bar and an opposing end of the second bar may comprise shaped bearings configured for bony elements of the spine. The first and second bar may be movable relative to each other between an open position and a closed position.

8 Claims, 3 Drawing Sheets

(56) References Cited

U.S. PATENT DOCUMENTS

| | | | |
|---|---|---|---|
| 2007/0270824 A1* | 11/2007 | Lim et al. .................... | 606/61 |
| 2007/0270827 A1* | 11/2007 | Lim et al. .................... | 606/61 |
| 2008/0033556 A1* | 2/2008 | Le Couedic et al. ....... | 623/17.16 |
| 2008/0177271 A1* | 7/2008 | Yeh .............................. | 606/90 |
| 2008/0208344 A1 | 8/2008 | Kilpela et al. | |
| 2008/0234824 A1* | 9/2008 | Youssef et al. ............. | 623/17.16 |
| 2008/0281423 A1 | 11/2008 | Sheffer et al. | |
| 2009/0149886 A1 | 6/2009 | Zentes et al. | |
| 2009/0209965 A1 | 8/2009 | Lewis | |
| 2009/0264929 A1 | 10/2009 | Alamin et al. | |
| 2009/0326589 A1* | 12/2009 | Lemoine et al. ............ | 606/280 |

FOREIGN PATENT DOCUMENTS

| | | | |
|---|---|---|---|
| WO | 2007127694 | A2 | 11/2007 |
| WO | 2008085445 | A2 | 7/2008 |
| WO | 2009036156 | A1 | 3/2009 |
| WO | 2009089123 | A1 | 7/2009 |
| WO | 2009117610 | A1 | 9/2009 |
| WO | 2009120855 | A1 | 10/2009 |

OTHER PUBLICATIONS

Office Action dated Mar. 28, 2013, issued by Canadian Intellectual Property Office regarding Canadian Patent Application No. 2775752, entitled Unloading-Dynamic Intervertebral Device; Applicant: LfC Spolka Z o.o.

Reply to Office Action dated Mar. 28, 2013, issued by Canadian Intellectual Property Office regarding Canadian Patent Application No. 2775752, entitled Unloading-Dynamic Intervertebral Device; Applicant: LfC Spolka Z o.o.; Reply filed Aug. 15, 2013.

Examination report dated Jun. 21, 2013, issued by European Patent Office regarding EPO Application No. 10 779 060.2-1506, entitled Unloading Dynamic Intervertebral Device; Applicant: LfC Spolka Z o.o.

Response to Examination report dated Jun. 21, 2013, issued by European Patent Office regarding EPO Application No. 10 779 060.2-1506, entitled Unloading Dynamic Intervertebral Device; Applicant: LfC Spolka Z o.o.; Response filed: Oct. 21, 2013.

Examination report dated Feb. 7, 2013, issued by the Intellectual Property Office of Singapore regarding SG Application No. 201202429-5, entitled Unloading Dynamic Intervertebral Device; Applicant: LfC Spolka Z o.o.

Response to Examination report dated Feb. 7, 2013, issued by the Intellectual Property Office of Singapore regarding SG Application No. 201202429-5, entitled Unloading Dynamic Intervertebral Device; Applicant: LfC Spolka Z o.o.; Response filed: Jul. 4, 2013.

Examination report dated Oct. 10, 2013, issued by the Intellectual Property Office of Singapore regarding SG Application No. 201202429-5, entitled Unloading Dynamic Intervertebral Device; Applicant: LfC Spolka Z o.o.

* cited by examiner

UNLOADING D-DYNAMIC INTERVERTEBRAL DEVICE

RELATED APPLICATIONS

This non-provisional patent application claims priority benefit with regard to all common subject matter of the earlier filed Polish Patent Application titled "Unloading-Dynamic Intervertebral Device", Polish Application Serial Number P-389241, filed on Oct. 9, 2009, which is hereby incorporated by reference in its entirety into the present application.

BACKGROUND

1. Field

Embodiments of the present invention relate to a device used in spinal surgery.

2. Related Art

Stabilizers used for interspinous spinal stabilization using a surgical posterior approach are usually known in the form of one or several cooperating carrying elements situated in the interspinous space, ended with profiled sockets for spinous processes. Such stabilizers situated in the axis of the spine serve mainly for one-level stabilization of the adjoining vertebrae.

Solutions are also known in the form of lamellar or rod bearing elements with an adjustable length, installed in the interspinous space and comprising hook elements resting against on spinous processes. Such stabilizers can be used for supporting the spine on one and several levels.

The solutions described above are additionally provided with elements attached to the bone using screws, pins, other mechanical latches or flexible ligaments. In most of such solutions, elements are supported in spinous processes and this requires using a bilateral surgical approach.

An interspinous implant situated non-axially in relation to the spine is known from the patent application WO2007/127550, comprising superior and inferior bearing elements cooperating in a sliding way along the axis corresponding to the axis of the spine. Laterally separated bearing elements are ended with brackets for fastening onto superior and inferior spinal interspinous processes, respectively. In a folded position, the device is of the height allowing its installation between spinal processes and the interspinous space is increased by distraction of both elements.

An axial interspinous implant in the form of a frame embracing exteriorly vertebral processes is disclosed in the patent application WO2007/127694. The frame is in the form of a ring or its parts provided with holes situated on both sides of the axis, through which elastic bands are drawn out. The bands constitute bearing elements pulling off superior and inferior processes respectively to the superior and inferior part of the frame. The place of connection of the implant with the bone can be secured by sharp projections constituting an integral part of internal surfaces of the frame.

From the patent application US 2006/0241614 an interspinous implant is known which contains a bearing supporting part with profiled sockets located axially between adjoining spinous process and two hook elements connected by an elastic band which passes through the support. The hooks fasten the processes from the superior side preventing excessive flexion of the spinal motion segment. The patent application WO 01/91658 discloses a device and the method of its application for distraction of adjacent spinous processes. The device has got a bracket with a guide fastened by a connector to a laterally separated rod element ended with hooks, which embrace spinous processes. The construction of the device allows rotational movement between the bracket and the hook.

A multi-segment stabilizer for controlling the intervertebral space is known from the U.S. Pat. No. 4,611,582. It comprises a longitudinal, laterally separated bearing body and two laminar clamps. The clamps are in the form of two alternating hooks, both adapted for a rigid, bilateral embrace of a part of one vertebra. The body is dual, consisting of movable cooperating parts connected with each other by threaded elements fastening and adjusting body's length.

The U.S. Pat. No. 5,439,463 refers to a spinal device which consists of two clamp elements ended with hook parts: a fixed one with a rod setting the distance and an adjustable one. The surface of the rod and the corresponding surface of the adjustable clamp cooperate in a sliding way through toothed surfaces, and their cooperation is secured by a distance fastening element provided with a clamping ring and threaded screw.

A device for implantation and distraction of spinal spinous processes is known from the patent application WO 2008/085445. It consists of a longitudinal body and two sliding elements. Each of them is composed of the main part cooperating with the body and hook arms for support on the bone. In an embodiment of the device, the arms are provided with a rough surface increasing friction in the area of contact of the implant and a spinous process.

All the solutions described above do not secure steady, even, and controlled intraoperative distraction, which is the essential purpose of the treatment of spinal dysfunctions. Corrective actions are performed after previously locating the implant in the interspinous space, thus necessitating acquisitions of a dimensional series of types of implants and precise selection of the implant's dimension for the interspinous space. Most of the solutions are intended for being fastened to biomechanically weak interspinous processes and they are designed only for such a fastening. The use of such solutions is also limited to only one segment of the spine, especially in the lumbar segment or on the lumbosacral border. Constructions used in the above described solutions are frequently complicated and made up of many elements. Thus a surgeon is forced to use a wide surgical approach and to adjust surgically the spinous processes to the bearing surface of the implant. Yet another inconvenience of the solutions referred to above is their great surgical invasiveness resulting from the necessity of dissection of soft tissues from both sides of the spine and also from the necessity of disrupting the supraspinous ligament or its separation from processes and withdrawing during installation of the implant.

SUMMARY

Embodiments of the present invention solve the above-mentioned problems and provide a distinct advance in the art of spinal surgery. Specifically, the present invention provides an unloading-dynamic intervertebral device. The device is used for an even, steady and adjustable decompression of the intervertebral interspinous space and for maintaining the distance between at least two vertebrae. The unloading-dynamic intervertebral device may also be used for the treatment of pathologic lateral deformations of the spine by supporting the device on bony elements of the posterior spinal column, especially on spinous processes and neural arches.

The unloading dynamic intervertebral device comprises a first bar and a second bar. The first bar may have a first end, a second end, and a guideline proximate the first end having an elongated gap formed therein. The second bar may have a first end, a second end, and a guide proximate the first end having at least one tang interposed within the elongated gap of the first bar, such that the first bar and the second bar are rotationally and slidably connected with each other about the tang. Alternatively, sliding-rotational and rotational cooperation of the first and second bars crossing in an open position may be realized by tangs situated on internal surfaces of the guideline and blind shaped gaps formed in the guide. The second end of the first bar and/or the second end of the second bar may comprise shaped bearings configured for bony elements of the spine at the second end. The first and second bar may be movable relative to each other between an open position and a closed position.

The guideline may also comprise two arms spaced apart from each other, with the guide disposed between the two arms. Furthermore, each of the arms may comprise an elongated gap and one or more tangs on the guide may be disposed within the elongated gaps. The device may also comprise a mechanism configured to block rotational movement of the first and second bars relative to each other when the first and second bars are in the closed position.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the preferred embodiments and the accompanying drawing figures.

BRIEF DESCRIPTION OF THE DRAWING FIGURES

Embodiments of the present invention are described in detail below with reference to the attached drawing figures, wherein.

Figure 1:
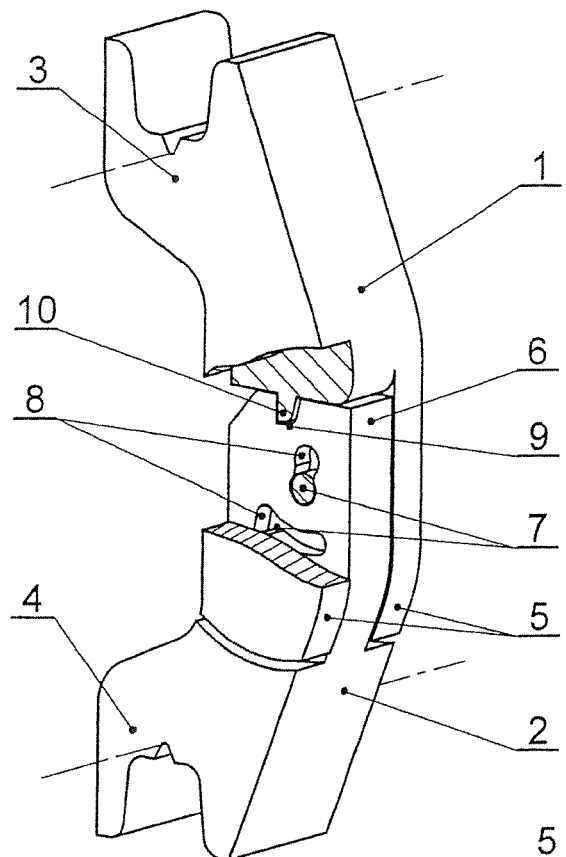
FIG. 1 is a perspective view of an unloading-dynamic intervertebral device constructed according to various embodiments of the invention.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

The scope of the invention is an unloading-dynamic intervertebral device, used in spinal surgery. The device is used for an even, steady and adjustable decompression of the intervertebral interspinous space and for maintaining the distance between at least two vertebrae, and also for the treatment of pathologic lateral deformations of the spine by supporting the device on bony elements of the posterior spinal column, especially on spinous processes and neural arches.

The unloading-dynamic intervertebral device is free of the above drawbacks. The unloading-dynamic intervertebral device may comprise two bars cooperating with each other, where each of them is needed from one side with a shaped bearing for bony elements of the spine. According to various embodiments of the invention, one of the bars is provided with a guideline and the other with a guide. Moreover, the first bar may be provided with at least one tang, situated in the corresponding shaped gap of the other bar, assuring rotatable and rotatable-sliding cooperation of the bars crossing in the open position of the device. The device may also be equipped with a mechanism blocking rotational movement of the bars in the closed position.

Depending on the construction of the device, there may be at least one shaped gap in the guide, and the guideline may be provided with at least one tang situated in the guide's gap. Alternatively, at least one shaped gap made in the guideline may cooperate with the ends of the tang fixed in the guide. In one embodiment of the device provided with a one-arm guideline, in the through hole of the guide there may be a tang fixed in the guideline. Conversely, the tang connected with the guide may be situated in the guideline.

A notch located in the end of the guide and a projection made in the guideline which cooperates with the guide may constitute the mechanism blocking rotational movement of the bars and their mutual location in the closed position of the device. In another embodiment, the mechanism blocking rotational movement of the bars in the closed position of the device may be formed by a projection made in the end of the guide cooperating with the notch made in the guideline. Depending on the construction of the device, the guide or the guideline may be provided with at least one shaped gap ended with a socket. The tang constituting an element of the mechanism blocking rotational movement of the bars in the closed position of the device may be situated in the socket.

The guideline or the guide of the device may have shaped gaps formed therethrough. The shaped gap may be connected with the input canal, thus enabling introduction of the tang. In one embodiment of the device, wherein shaped gaps are made in the guideline, the mechanism blocking rotational movement of the bars in the closed position of the device may comprise a plate situated in the shaped gaps of the two-arm guideline. In this embodiment, a pin setting the mutual position of the guide and the guideline may constitute the mechanism blocking movement of the bars in the closed position.

In some embodiments of the invention, at least one shaped bearing may constitute a separate element moveably connected to the corresponding bar. For a better adjustment of the device to the construction of bone elements of the patient's spine, at least one bearing may be provided with at least one incision, thus imparting resilience to the construction.

The device may be provided with a scale showing the value of distraction, which will be obtained in the closed position of the device. For securing the position of the device in the patient's body, the bars of the device may be provided with at least one means for guiding the band.

The unloading-dynamic intervertebral device is used to support dysfunctions of any spinal segment, including also deformities. The device can be used at one or many levels with unilateral or bilateral support on spinous processes and/or simultaneously on bony elements adjoining the spinous processes, such as neural arches. The device offers the possibility of steady and even intervertebral distraction during the process of installation between bony elements, which is not possible in other solutions, it decreases the risk of an incorrect selection of implant's dimensions, excludes the use of additional surgical instruments, such as distracters, and decreases the load on tissues included in stabilization. Owing to mutual mobility of interconnected arms, possibilities of their angular alignment and thanks to an adjustable point of rotation, the device assures an adjustable range of distraction with the use of only one device, without the necessity of a full dimensional series.

Application of multilevel stabilization allows distribution of loads on a greater surface and a longer spinal segment, and it also improves spinal biomechanics. Stabilization of many spinal levels affects unloading dysfunctional vertebrae, which can be additionally supported by employing other ways of stabilization. The device and the method of its implantation are characterized by small invasiveness, unilateral surgical approach, allowing for retainment of the supraspinous ligament, which is important in stabilizing the posterior spinal column. In some cases, justified by the clinical condition, the device can also be used bilaterally. Implantation of the device is easy and quick, thus affecting the duration of surgery and can be realized in variants, depending on restrictions of the operating field following from the level and anatomy of the osteoarticular system being stabilized.

Depending on the manner of cooperation with the bone on which the implant is resting, the plane of closing the device by rotational and rotational-sliding movement can be approximate to the sagittal plane of the spine or can be inclined to it at an angle of 90°, which gives an operating surgeon greater possibilities of installation. The construction and dimensions of the device offer possibilities of treating patients from various age groups.

Figure 2:
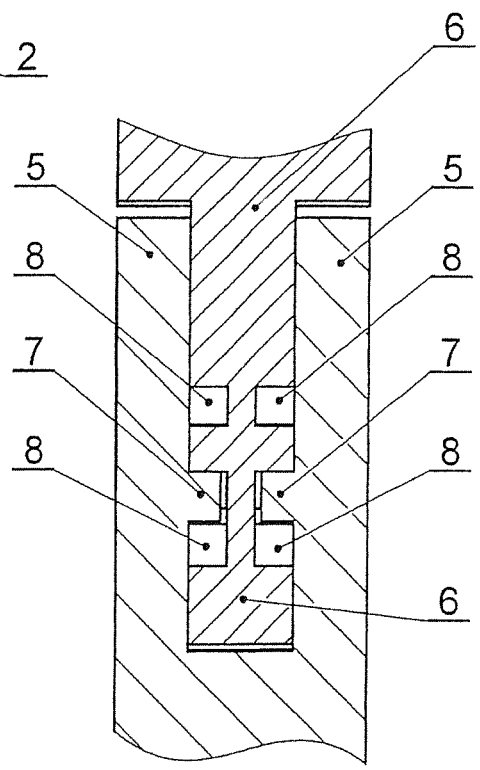
FIG. 2 is a cross sectional, fragmentary view of a movable connection of bars of the device of FIG. 1.
Figure 3:
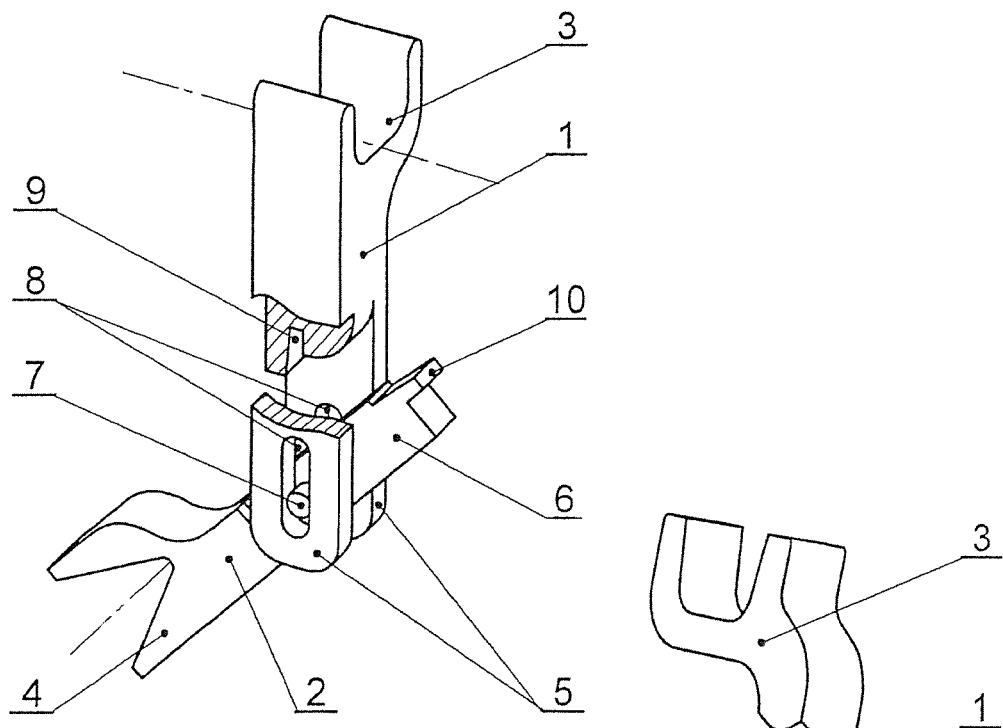
FIG. 3 is a perspective view of an embodiment of the device in an open position with perpendicular orientation of bearings and a part section depicting a blocking mechanism.
Figure 4:
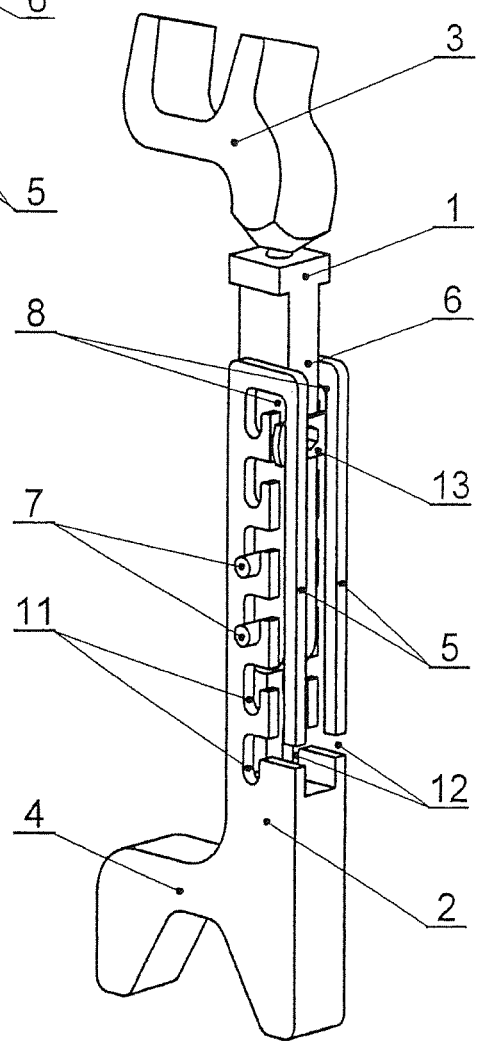
FIG. 4 is a perspective view of an embodiment of the device with shaped gaps provided with sockets and a movable bearing and plate of the blocking mechanism.
Figures 5, 6:
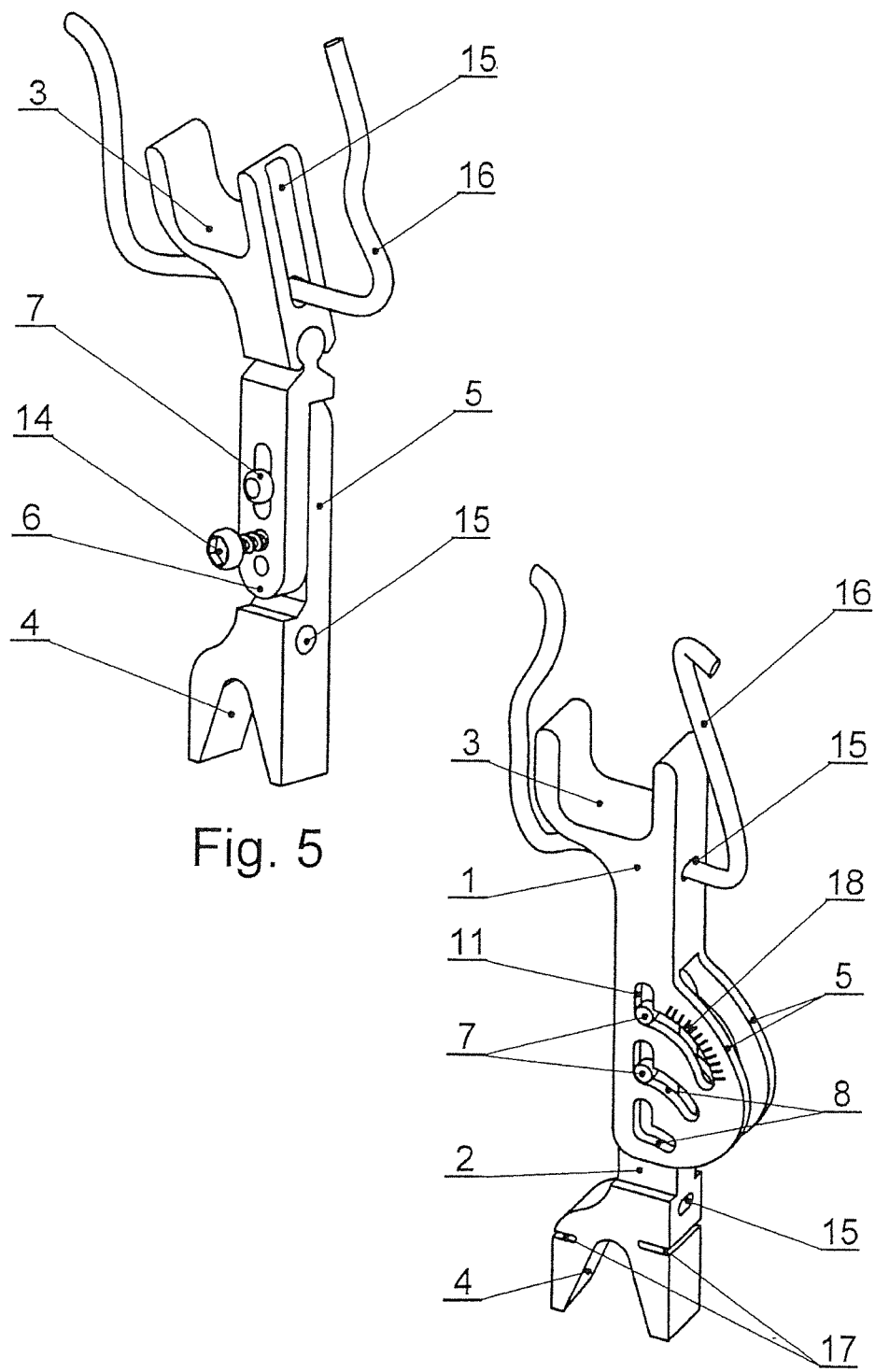
FIG. 5 is a perspective view of an embodiment of the device with a one-arm guideline, blocking mechanism in the form of a pin and clamping band.
FIG. 6 is a perspective view of an embodiment of the device equipped with a scale and incisions in the bearing.

The device is presented in examples of several embodiments in the accompanying figures, wherein FIG. 1 illustrates one embodiment of the device depicting elements of the blocking mechanism; FIG. 2 shows in the section a fragment of the movable connection of the bars; FIG. 3 illustrates one embodiment of the device in axonometric projection in an open position with perpendicular orientation of bearings and a part section depicting the blocking mechanism; FIG. 4 illustrates an axonometric projection one embodiment of the device with shaped gaps provided with sockets and the movable bearing and plate of the blocking mechanism; FIG. 5 illustrates an axonometric projection one embodiment of the device with the one-arm guideline, blocking mechanism in the form of a pin and clamping band, whereas FIG. 6 presents in axonometric projection an embodiment of the device equipped with a scale and incisions in the bearing.

The unloading-dynamic intervertebral device may comprise two movable cooperating bars 1,2, whose implantation in the area of spinal dysfunction consists in passing from the open position to closed position making use of the simultaneous displacement of bony elements during distraction. Each bar 1,2 may be ended from one side with a shaped bearing 3,4 for vertebral bony elements, such as: the spinous process or the neural arch. For the other end, one of the bars—bar 1—may be ended with a two-arm guideline 5, whereas the other bar—bar 2—may be ended with a guide 6. Sliding-rotational and rotational cooperation of bars 1,2 crossing in an open position may be realized by: tangs 7 situated on internal surfaces of guideline 5 and blind shaped gaps 8 in guide 6, as shown in FIG. 2.

In a closed position of the device, the reverse movement of bars 1, 2 may be blocked by a blocking mechanism. This mechanism may comprise notch 9 situated on the end of guide 6 and projection 10 made in the guideline 3 cooperating with it. In one embodiment of the invention shown in FIG. 3, notch 9 is made in guideline 3, whereas projection 10 comprises a constructional fragment of the end of guide 6. Sliding-rotational and rotational cooperation of bars 1,2 which cross with each other in the open position may be realized by the ends of tang 7 fastened in guide 6 which cooperate with two through shaped gaps 8 made in the guideline 5. Moreover, variously oriented bearings 3,4 may allow the device to rest at the same time on the spinous process of one vertebra and the neural arch of the other vertebra.

In one embodiment of the invention illustrated in FIG. 4, shaped gaps 8 in the guideline 5 are provided with sockets 11 situated in pairs and cooperating with two tangs 7 situated in the guide 6. Such a configuration may constitute the mechanism blocking the sliding-rotational movement of bars 1,2 and assure an adjustable range of distraction with the use of only one device, without the necessity of having a full series of dimensions. To facilitate the introduction of the tang 7, shaped gaps 8 may be provided with an input canal 12.

The device may also be provided with an additional mechanism blocking the rotational movement of bars 1,2 in the closed position in the form of a plate 13 located in gaps 8 of the two-arm guideline 5 and rested on the guide, as shown in FIG. 4. For a better adjustment to bony elements in various parts of vertebrae, it may be preferable to apply the movable connection of at least one bar 1 with the bearing 3. Elements of the connection may constitute a three-dimensional joint, as in FIG. 4 or a flat one, as shown in FIG. 5.

In one embodiment of the device according to the invention illustrated in FIG. 5, a threaded pin 14 passing through the one-arm guideline 5 and guide 6 constitutes the blocking mechanism. The device may be provided with means 15 that guide band 16, which secures the device against shifting in the patient's body, thanks to its fixation to bony elements. In one embodiment of the device illustrated in FIG. 6, the bearing 4 is provided with two incisions 17 increasing its resilience and giving the device dynamic features. The device may be equipped with scale 18 of angular arrangement of bars 1,2 in an open position, which provides information about the range of distraction in the closed position of the device.

Although the invention has been described with reference to the preferred embodiment illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. An unloading dynamic intervertebral device comprising two bars cooperating with each other, where each of said bars is ended on one side with a shaped bearing for bony elements of the spine and comprises a distal side end that is located distal from said shaped bearing, wherein
one of the bars (1,2) is provided with a two arm guideline (5) including two arms that extend towards the distal end of the bar and a space extending between the arms and forming a recess extending from said distal end towards said shaped bearing and ending in a bottom forming a recess bottom, and
the other of the bars (1,2) is provided with a guide (6) comprising at least one wall having a width to fit between said arms of the two-arm guideline (5), said wall having a top end forming a guide top wherein either the arms of the two-arm guideline (5) are provided with at least one tang (7) and the wall of the guide (6) is provided with a shaped gap (8), or the wall of the guide (6) is provided with at least one tang (7) and the arms of the two-arm guideline (5) are each provided with a shaped gap (8),
wherein said tang (7) is situated in said shaped gap (8), such that it allows rotation of the bars about the tang (7) as an axis of rotation such that the bars cross with each other in an open position of the device and such that the top end of said wall shows towards said recess bottom in a closed position of the device,
wherein the shaped gap (8) is configured to allow sliding of the tang within the shaped gap perpendicular to the axis of rotation, such that a location of a point of rotation between the bars (1,2) is adjustable,
wherein the unloading dynamic intervertebral device further comprises a mechanism blocking rotational movement of the bars (1,2) in a closed position of the unloading dynamic intervertebral device, the mechanism blocking rotational movement of the bars (1,2) comprising a first part located at said recess bottom and a second part located at said guide top.

2. The device according to claim 1 wherein at least one shaped gap (8) is made in the guide (6), wherein the guideline (5) is provided with at least one tang (7) situated in the gap (8) of the guide (6).

3. The device according to claim 1 wherein at least one shaped gap (8) is made in the guideline (5), and ends of the tang (7) fixed in the guide (6) cooperate with the gap.

4. The device according to claim 1 wherein said first part of said mechanism blocking rotational movement of bars (1,2) in the closed position comprises a projection (10) and said second part comprises a notch (9).

5. The device according to claim 1 wherein the mechanism blocking rotational movement of the bars (1,2) in the closed position of the device comprises: a projection (10) situated on the end of the guide (6) which cooperates with the notch (9) made in the guideline (5).

6. The device according to claim 1 wherein the shaped gap (8) is formed through one of the bars (1,2).

7. The device according to claim 1 wherein at least one bearing (3,4) is provided with at least one incision (17).

8. A method for spinal adjustment using an unloading dynamic intervertebral device comprising: a first bar having a first end and a second end, the first bar comprising:
a guideline proximate the first end of the first bar having a recess extending from said first end towards said second end, said recess comprising a bottom, and a shaped bearing configured for bony elements of the spine at the second end of the first bar; and a second bar having a first end and a second end, the second bar comprising: a guide proximate the first end of the second bar, said guide having a top end dimensioned to fit within said recess, and a shaped bearing configured for bony elements of the spine at the second end of the second bar, one of said first and second bar having at least one elongated gap formed therein, the other of said first and second bar having at least one tang interposed within the at least one elongated gap, such that the first bar and the second bar are rotationally and slidably connected with each other about the at least one tang, said tang capable of being used as an axis of rotation, and a rotational blocking mechanism comprising a first part proximal to said recess bottom and a second part proximal to said guide top the method comprising:
mating the shaped bearing of the first bar with at least a first vertebrae of a spine;
mating the shaped bearing of the second bar with at least a second vertebrae of the spine;
slidably and rotatably adjusting the first bar about the at least one tang, wherein said bars may be operated in a scissors like action with respect to each other, until a desired spacing between the first and second vertebrae is achieved, wherein sliding the first bar relative to the at least one tang adjusts a location of a point of rotation of the first bar relative to the second bar, allowing for an adjustable range of distraction; and
fixing the first bar relative to the second bar when the desired spacing between the first and second vertebrae is achieved.

* * * * *